United States Patent [19]

Hasegawa et al.

[11] Patent Number: 4,860,732

[45] Date of Patent: Aug. 29, 1989

[54] ENDOSCOPE APPARATUS PROVIDED WITH ENDOSCOPE INSERTION AID

[75] Inventors: Hiroshi Hasegawa; Hirofumi Miyanaga, both of Hachioji, Japan

[73] Assignee: Olympus Optical Co., Ltd., Tokyo, Japan

[21] Appl. No.: 275,499

[22] Filed: Nov. 23, 1988

[30] Foreign Application Priority Data

| | | | |
|---|---|---|---|
| Nov. 25, 1987 | [JP] | Japan | 62-296725 |
| Feb. 8, 1988 | [JP] | Japan | 63-26840 |
| Feb. 8, 1988 | [JP] | Japan | 63-26841 |

[51] Int. Cl.[4] .................. A61B 1/06

[52] U.S. Cl. .................. 128/6; 356/241

[58] Field of Search .................. 128/4, 6; 350/96.26; 73/151; 356/241

[56] References Cited

U.S. PATENT DOCUMENTS 4,676,230 6/1987 Miyazaki .................. 128/4

FOREIGN PATENT DOCUMENTS 62-33021 2/1987 Japan .

60-26923 2/2985 Japan .

*Primary Examiner*—William H. Grieb

*Attorney, Agent, or Firm*—Armstrong, Nikaido, Marmelstein, Kubovcik & Murray

[57] ABSTRACT

In an endoscope apparatus, an optical end adapter is detachably attached to the end portion of an elongated inserting section, and an endoscope insertion aid is detachably provided which has the minimum diameter which is smaller than the maximum outer diameter of the optical end adapter. The endoscope insertion aid is fitted onto the inserting section from the leading end thereof, and then the optical end adapter is attached. It is, accordingly, possible to positively prevent the endoscope insertion aid from coming off the optical adapter.

17 Claims, 11 Drawing Sheets 3
15
8
9
20
19
16
10
4
CONTROL APPARATUS
7
10a
5
116
2
1
13
22
6
14
12
11
21

ENDOSCOPE APPARATUS PROVIDED WITH ENDOSCOPE INSERTION AID

BACKGROUND OF THE INVENTION

FIELD OF THE INVENTION

The present invention relates to an endoscope apparatus provided with means for detecting in advance whether or not an insertion aid is loose.

In recent years, medical endoscopes of the type whose elongated inserting section can be inserted into a living body so as to make a diagnosis have been widely used. In addition, industrial endoscopes have been widely used of the type whose elongated inserting section is inserted into a tube of a boiler, a turbine or the like to inspect the interior thereof.

In general, such an industrial endoscope is applied to various portions each having a different size, and if the inner diameter of the inserting end portion of the endoscope greatly differs from the inner diameter of a portion into which it is inserted, the inserting section of the endoscope apparatus greatly fluctuates within the portion into which it has been inserted. As a result, the direction of observation is difficult to fix exactly. Also, if the outer diameter of the inserting end portion is larger than the diameter of the portion into which it is inserted, the inserting end portion may be inclined downwardly in that portion. As a result, a bottom wall of the portion may only be observed.

To solve the above-described problems, the present applicant proposed endoscope apparatus of the type whose endoscope is provided with an insertion aid.

In the conventional example shown in, for example, Japanese Patent Laid-open No. 26923/1985, means for attaching an insertion aid to an inserting section, a member of an insertion aid is fixed in the inserting section of an endoscope by press fitting.

U.S. Pat. No. 4,676,230 (Japanese Patent Laid-open No. 183615/1986) and Japanese Utility Model Laid-open No. 33021/1987 propose endoscope apparatus of the type in which the aforementioned attaching means is such that a member of an insertion aid is engaged with a threaded portion which is formed around the leading end portion of an endoscope, the attaching means further having the function of preventing the insertion aid from coming off by forming a projection in the circumferential direction.

The former one of the above-described conventional examples has the disadvantage that since it is difficult to positively fix the insertion aid, the insertion aid tends to easily come off. In addition, it is difficult to detect in advance whether or not the state of attachment of the insertion aid is loose.

The latter conventional example has the disadvantage that, although a mechanism for preventing an insertion aid from coming off is provided, even if the insertion aid is loose, it is difficult for an endoscope operator to detect that fact.

Should the insertion aid come off in a boiler, an engine or the like, it will be difficult to eliminate the insertion aid to the exterior. In addition, if the insertion aid which has come off is left there, the boiler, the engine or the like may fail, thus resulting in serious accidents.

SUMMARY OF THE INVENTION

It is therefore an object of the present invention to provide an endoscope apparatus which is arranged so that whether or not the state of attachment of an insertion aid is loose can be detected before the insertion aid comes off.

It is another object of the present invention to provide an endoscope apparatus in which safety in operation can be enhanced since an insertion aid can be prevented from coming off.

To achieve the above and other objects, in accordance with the present invention, an endoscope insertion aid of cylindrical configuration is attached to the leading end of the inserting section of an endoscope, and then an optical end adapter is attached to the leading end portion of the inserting section. The optical end adapter serves to prevent the endoscope insertion aid from coming off. In addition, the optical end adapter is fixed by screwing and, if the screwing becomes loose, an abnormal portion appears in a displayed endoscopic image owing to the offset between the optical axis of the optical system of the optical end adapter and the optical axis of the optical system of the inserting end portion and it is, accordingly, possible to detect the fact that the state of attachment of the optical end adapter is not correct.

DESCRIPTION OF THE PREFERRED EMBODIMENTS

Figure 2:
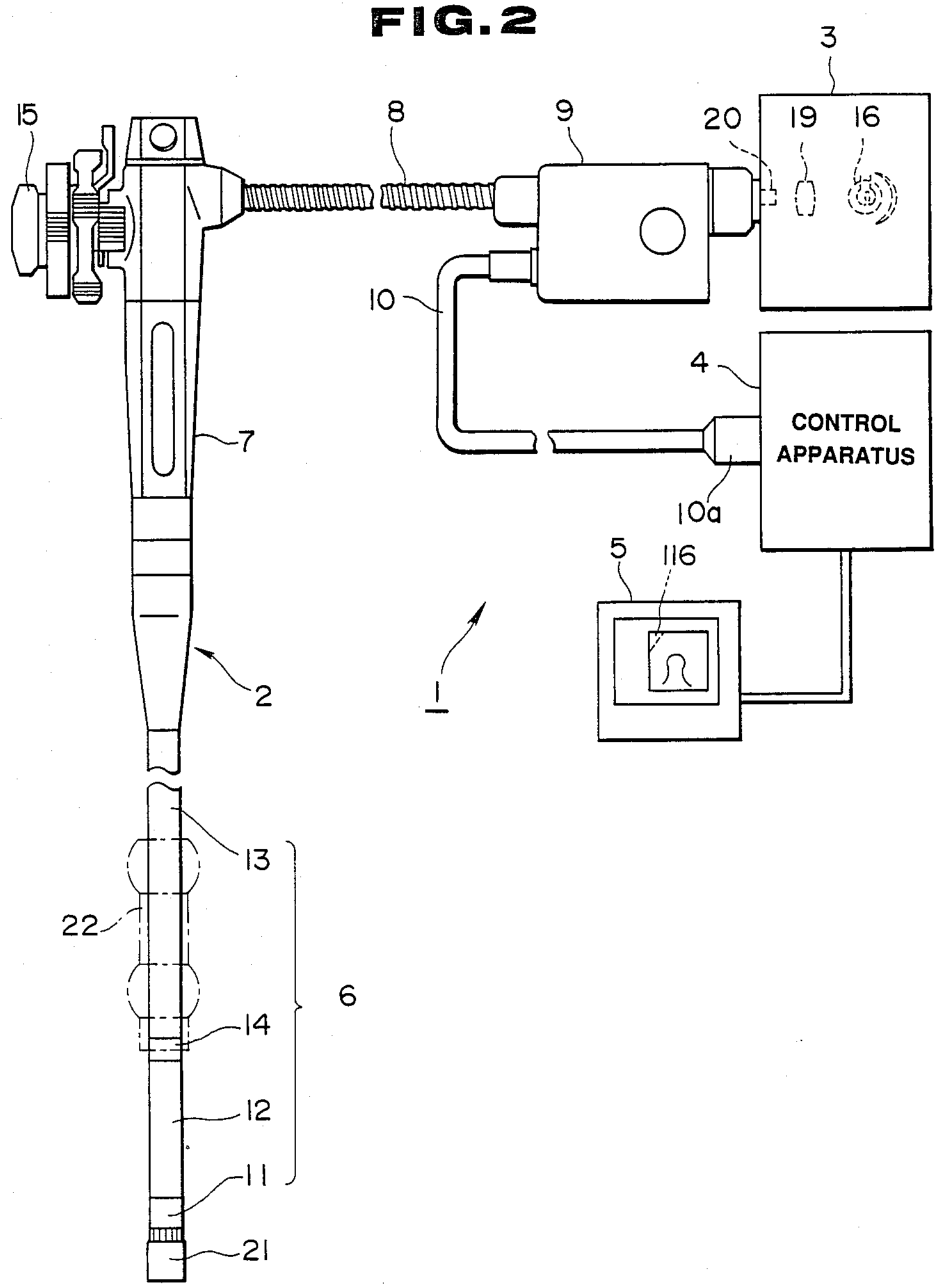
FIG. 2 is a diagrammatic view showing the construction of the whole of the first embodiment.

As shown in FIG. 2, an endoscope apparatus 1 according to a first embodiment of the present invention includes an electronic endoscope 2, a light source 3 for supplying illuminating light to the electronic endoscope 2, a control apparatus 4 for processing image signals transmitted from the electronic endoscope 2, and a color monitor 5 having a display screen and arranged to display the video signals output from the control apparatus 4 on the display screen.

The electronic endoscope 2 is provided with an elongated inserting section 6, an operating section 7 connected to the rear end (the upper end as viewed in FIG. 2) of the inserting section 6 and having a large diameter, a universal cord 8 extending from one side of the operating section 7, and a signal cable 10 extending from a light source connector 9 attached to the universal cord 8.

The front end (the lower end as viewed in FIG. 2) of the inserting section 6 is provided with a hard end portion 11, and a flexible section 12 capable of being curved is connected to the rear end of the end portion 11 (the upper end as viewed in FIG. 2). A soft section 13 having flexibility is connected to the rear end of the flexible section 12. An insertion-aid mounting portion 14 is provided around the outer periphery of the inserting section 6 which is adjacent to the boundary between the flexible section 12 and the soft section 13.

The flexible section 12 is capable of being freely curved in all directions by operating a curving knob 15 provided on the operating section 7.

The light source connector 9 is, as described above, connected to the light source 3, and the white light of the light source lamp 16 is focused on the entrance end surface of a light guide 20 by a condenser lens 19.

The signal cable 10 which extends from the light source connector 9 has a signal connector 10*a* at the other end, and the signal connector 10*a* can be connected to the control apparatus 4. Image signals obtained by imaging in the electronic endoscope 2 are supplied to the control apparatus 4, converted into predetermined video signals through signal processing, and transmitted to the color monitor 5. Thus, an image to be observed is displayed in color.

An optical end adapter 21 made of a hard material and having an approximately columnar configuration can be detachably attached to the end portion 11 of the inserting section 6.

Figure 3:
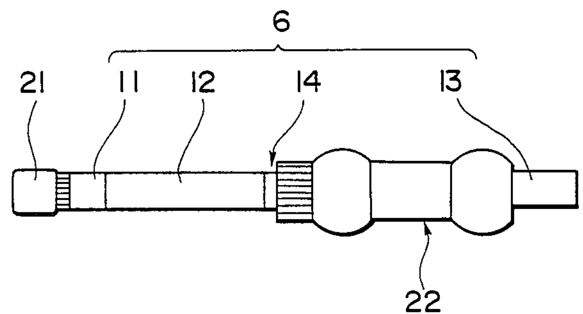
FIG. 3 is a side elevational view showing the insertion aid attached to the inserting section according to the first embodiment.

An inserting aid 22 (for an endoscope) can be attached to the insertion-aid mounting portion 14. FIG. 3 shows a portion of the inserting section 6 to which the insertion aid 22 is attached, and FIG. 1 shows on an enlarged scale the portion shown in FIG. 3.

Figure 1:
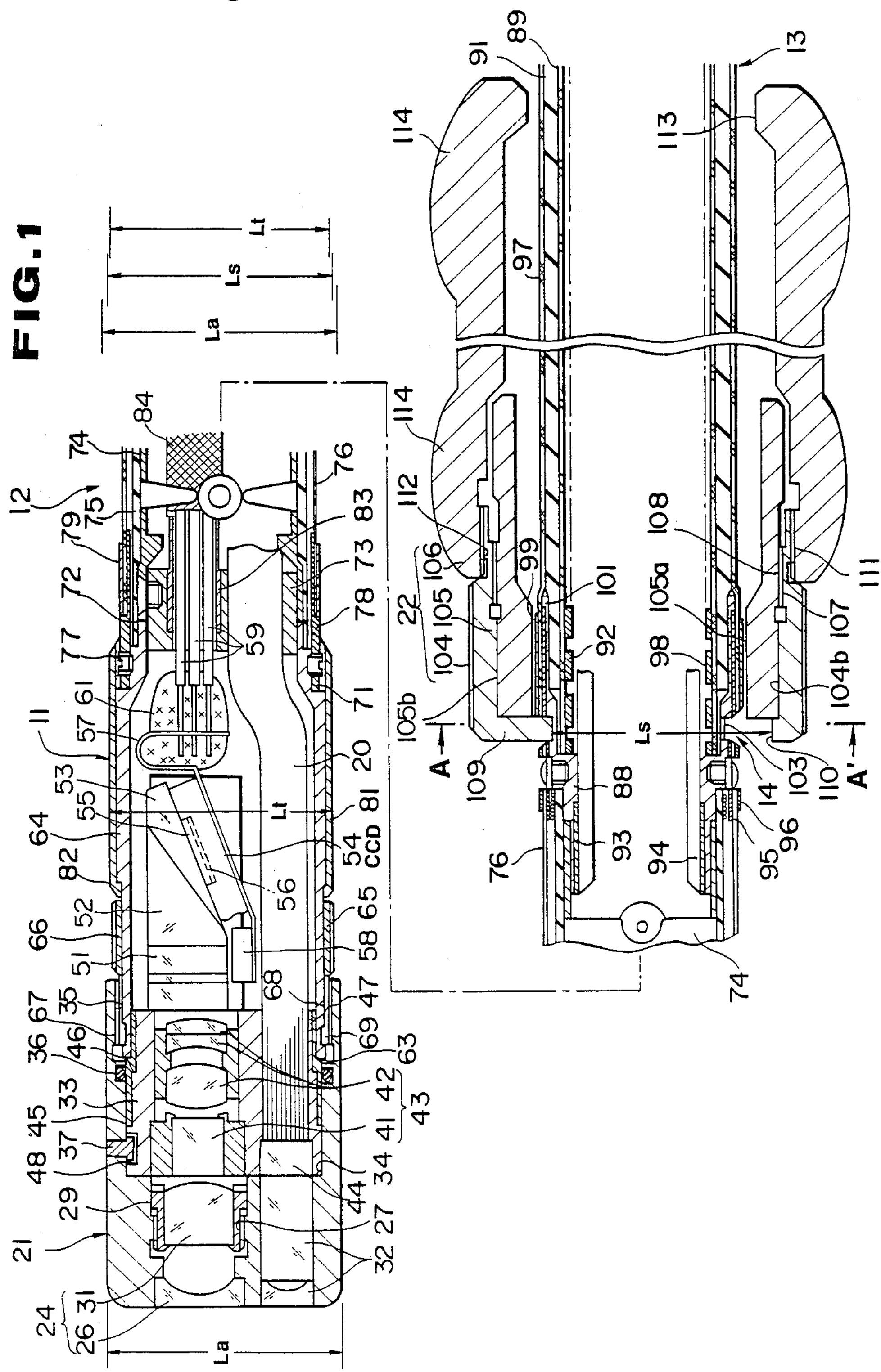
FIG. 1 is a longitudinal sectional view of a first preferred embodiment of the present invention, and shows the inserting section of an endoscope provided with an insertion aid.

As shown in FIG. 1, the leading end surface of the optical end adapter 21 has an observation through-hole for allowing observation and illumination through-holes for allowing projection of illuminating light, and these through-holes are formed in parallel with the longitudinal axis of the inserting section 6.

A first lens 26 which serves as an optical member constituting part of a view-angle changing lens system 24 is fitted into the leading end portion of the observation through-hole. A second lens 31 which constitutes part of the view-angle changing lens system 24 is disposed rearwardly of the first lens 26. The second lens 31 is fitted into a lens frame 29 which has an externally threaded portion which is screwed into an internally threaded portion which is formed around the inner periphery of the observation through-hole.

Figure 4:
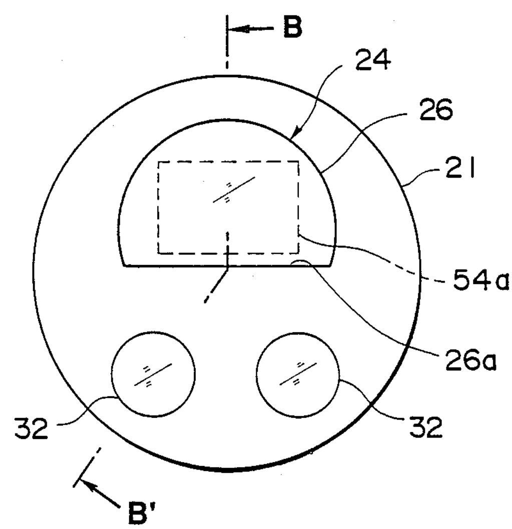
FIG. 4 is a front elevational view of an optical end adapter attached to the end portion used in the first embodiment.

As shown in FIG. 4, two illumination through-holes are formed and a projection lens system 32 is fixed in each of the illumination through-holes.

As shown in FIG. 1, the rear end of the optical end adapter 21 has a recess 34 which has a circular shape in cross section and which is capable of receiving an approximately columnar, front end body 33 of the electronic endoscope 2. Thus, the center line of the optical end adapter 21 can be aligned with that of the inserting section 6. A threaded portion 35 is formed around a rear portion of the inner periphery of the recess 34. An annular groove is formed around an inner periphery forward of the recess 34. An annular groove is formed around an inner periphery forward of the threaded portion 35, and an annular liquid-tight member 36 such as an O ring is fitted into the annular groove. A positioning pin 37 projects radially inwardly at a location forward of the annular groove.

The front end body 33 which is inserted in the recess 34 has an observation through-hole for allowing observation and illumination through-holes for allowing projection of illuminating light, and these through-holes are formed in parallel with the longitudinal axis of the inserting section 6. An optical rod 41 is mounted on a first lens frame attached to the inner periphery of the observation through-hole, and a second lens system 42 is mounted on a second lens frame attached to the portion of the inner periphery which is rearward of the optical rod 41. The optical rod 41 and the second lens system 42 constitute an objective lens system 43. A cover glass 44 is fitted into the front end portion of the illuminating through-hole and, the rear end surface of the cover glass 44 abuts against and is fixed to the exit end surface of the light guide 20 which is inserted through the inserting section 6.

Figure 5:
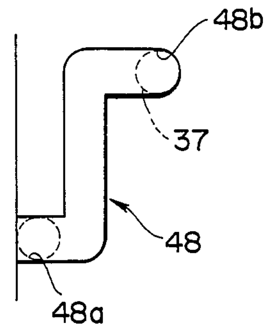
FIG. 5 is a developed view of a positioning groove formed in the end portion.

A step 45 and a step 46 are formed in the outer periphery of the front end body 33 in such a manner that the outer diameter of the body 33 decreases rearwardly in a stepwise manner. A cylindrical prism frame 47 has an outer diameter which is identical to the outer diameter of the front body 33, and is fitted onto the small diameter portion oh the front end body 33 to a position at which the front end of the prism frame 47 abuts against the step 45. The prism frame 47 is fixed to the front end body 33 by means of a screw (not shown). A positioning groove 48 of crank-like shape, as shown in FIG. 5, is formed in the outer periphery of the front end of the front end body 33. The positioning pin 37 is guided along the positioning groove 48 from a start position 48*a* to an end position 48*b*, and the front end body 33 is positioned at the end position 48*b*.

A prismatic optical low-pass filter 51, a first prism 52 and a second prism 53 are held in the rear end portion of the prism frame 47 in that order from the front side, and the first and second prisms 52 and 53 serve as a light transmitting means.

The optical low-pass filter 51 is disposed such that its front and rear end surfaces are normal to the optical axis of the objective lens system 43. Light which has passed through the optical low-pass filter 51, the first prism 52 and the second prism 53 is transmitted to a CCD 54 whose imaging surface is tightly attached to the exit end surface of the second prism 53.

The CCD 54 is inclined with respect to the longitudinal axis of the inserting section 6. A color filter array 56 covered with a sealing glass 55 is attached to the front of the imaging surface of the CCD 54. The color filter array 56 separates incident light into red, green and blue for each pixel.

The reverse side of the CCD 54 is attached to a flexible circuit board 57, and an electronic part 58 is mounted on the portion of the flexible circuit board 57 which is forward of the CCD 54. A plurality of signal lines 59 are soldered to the portion of the flexible circuit board 57 which extends rearwardly of the CCD 54, and this portion is bent and covered by a reinforcement member 61, such as an electrically insulating adhesive.

FIG. 4 shows the state wherein the optical end adapter 21 is attached to the end member 11. As illustrated, the first lens 26 which constitutes part of the view-angle changing lens system 24 has a semicircular shape having a cutaway portion 26*a*. The cutaway portion 26*a* is formed by cutting the portion of the first lens 26 which is located toward the center line of the optical end adapter 21. FIG. 1 shows a cross-sectional view, taken along line B—B′ of FIG. 4. If the optical end adapter 21 is correctly attached (as shown in FIG. 1), the cutaway portion 26*a* is, as shown in FIG. 4, located in parallel with one side of the rectangular shape of an image area 54*a* of the CCD 54. Therefore, when an optical image of an object is passed through the view-angle changing lens system 24 and the objective lens system 43 and focused on the image area 54*a* of the CCD 54, the cutaway portion 26*a* does not exert any influences upon the inside of the image area 54*a* if the optical end adapter 21 is correctly attached to the end member 11. On the other hand, if the optical end adapter 21 is loosely attached to the end member 11, then the optical end adapter 21 is circumferentially inclined from its correct position and thus the cutaway portion 26*a* overlaps the visual field of the image area 54*a*. Accordingly, an observer can check whether the optical end adapter 24 is attached correctly or loosely, that is, whether the optical end adapter 24 is likely to come off, by observing the image formed on the image area 54*a* of the CD 54. In addition, if the state of attachment of the optical end adapter 24 is not correct, light to be observed is not perfectly incident, from the optical end adapter 21, upon the objective lens system 43 in the endoscope 2. As a result, since a part of the light is cut off and the visual field becomes partially dark, the observer can check the state of attachment of the optical end adapter 21.

As shown in FIG. 1, the rear portion of the outer periphery of the prism frame 47 which follows the step 46 is formed into a small diameter portion 63. The small diameter portion 63 is fitted into the front end portion of a cylindrical cover member 64 for accommodating the flexible circuit board 57 and the CCD 54 mounted on the flexible circuit board 57. The cover member 64 has a step which is formed around the mid portion on its longitudinal axis, and the portion forward of the step is formed into a small diameter portion 65. An attachment ring 66 on which the optical end adapter 21 is mounted is rotatably fitted onto the outer periphery of the small diameter portion 65. A slit is formed in a front portion of the attachment ring 66, and an externally threaded portion 67 is formed around the outer periphery of the front portion of the attachment ring 66. Thus, the externally threaded portion 67 of the attachment ring 66 is screwed into an internally threaded portion 68 formed around the inner periphery of a rear end portion of the optical end adapter 21. A projection 69 is formed on the inner periphery of the front portion of the attachment ring 66, and the projection 69 can engage with a recess formed in the outer periphery of the cover member 64 that is adjacent to the front end thereof.

A small diameter portion 71 is formed around a rear portion of the cover member 64 and an even smaller diameter portion 72 is formed rearward of a step. A cylindrical ring stopper 73 having through-holes for receiving the signal cables 59 and a through-hole for receiving the light guide 20 is fitted into a rear portion of the inner periphery of the cover member 64. Approximately annular joint pieces 74 are rotatably connected together in side-by-side relationship along the longitudinal axis of the inserting section 6, and the joint piece at the leading position is fitted onto and fixed by a screw to the portion of the ring stopper 73 which projects rearwardly of the cover member 64.

The joint pieces 74 are covered with a flexible tube member 75, and the front end of the tube member 75 is fitted onto the small diameter portion 72 and covers it. Further, the outer periphery of the tube member 75 is covered with a protecting sheath 76 constituted by a mesh tube which is composed of braided metal wires.

The front end portion of the protecting sheathe 76 is fitted onto the small diameter portion of a fixing ring 78 (which is fitted onto a small diameter portion 71 of the rear of the cover member 64 and which is fixed to the small diameter portion 71 by a screw 77). Further, a stop ring 79 is fitted onto and fixed, as by soldering, to the outer periphery of the front end of the protecting sheathe 76.

A cylindrical stopper member 81 for preventing the screw 77 from coming off is fitted with a play onto the outer periphery which includes the outer periphery of the cover member 64 as well as the outer peripheries of the fixing ring 78 and the screw 77. The outer diameter of the stopper member 81 is equivalent to that of the attachment ring 66. A projection 82 is formed around the inner periphery of the stopper member 81 and is capable of engaging with the step which is formed on the cover member 64.

The outer diameters of rear portions of the aforementioned through-holes for receiving the signal cables 59 are enlarged in a stepwise manner, and a ring-shaped cable stopper 83 is fitted onto and fixed to the enlarged portion. A rear end portion of the cable stopper 83 is formed into a small diameter portion, and a shield code 84 which includes and covers the signal cables 59 is fixed to the rear end portion with electrical conductivity maintained, as by soldering.

The opposite ends of the tube member 75 are wound with, for example, strings and fixed by an adhesive so that they may be kept liquid-tight. The joint piece 74 at the trailing position is bonded, as by an adhesive, to a connector 88 made of a hard material and having an approximately cylindrical shape.

The rear end portion of the connector 88 is fitted onto the front end portion of a flexible tube 91 which is composed of a braided tube 89 and a resin coating which covers the braided tube 89. A spiral tube 92 having flexibility and formed by spirally winding an elongated thin sheet material is provided around the inner periphery of the braided tube 89. The light guide 20 and the signal cables 59 are inserted through the spiral tube 92. A cylindrical member 93 is bonded to the inner periphery of the front end portion of the connector 88, as by an adhesive. An elongated pipe 94 is fixed, as by brazing, to the inner periphery of the cylindrical member 93. It is to be noted that, although not shown, an angle wire is inserted through the pipe member 94.

The outer periphery of the protecting sheathe 76 which covers the flexible section 12 is clamped between an inner tube 95 and an outer tube 96 at the position of the outer periphery of the connector 88 and fixed to the connector 88 by a screw.

At the location of the soft section 13 as well, the outer periphery of the flexible tube 91 is coated with an sheathe 97 composed of a braided tube or the like.

The sheathe 97 is impregnated with a fluoro rubber, and the front end of the sheathe 97 is clamped between the inner tube 98 and the outer tube 99.

A large diameter portion 101 is formed in the rear end of the outer periphery of the connector 88. When the protecting sheathe 97 of the soft section 13 is pressed rearwardly, the large diameter portion 13 serves as a stopper for the inner tube 98 and fixes the sheathe 97 of the soft section 13.

An annular recess 103 is formed around the outer periphery of the connector 88 at a location between the rear end of the sheathe 76 for protecting the flexible section 12 and the front end of the sheathe 97 for protecting the soft section 13. Thus, the insertion-aid mounting portion 14 is formed.

The insertion aid 22 which will be described below can be mounted on the above recess 103.

The insertion aid 22 is constituted by a stopper 104, a stopper support 105, and a cover member 106. The stopper support 105 is composed of a cylindrical member having an engagement hole **105*a* which can be fitted from the end portion 11 onto the soft section 13 and which can be fitted onto the outer tube 99 with a play. An externally threaded portion 107 onto which the stopper 104 is fitted is formed around the outer periphery of the stopper support 105. An internally threaded portion 108 for enmeshment with the externally threaded portion 107 is formed around the inner periphery of the stopper 104. An engagement portion 105*b* which is fitted into the stopper 104 is formed around the outer periphery of the portion of the stopper support 105 which is forward of the externally threaded portion 107. An engagement hole 104*b* which engages with the engagement portion 105*b* is formed around the inner periphery of the stopper 104. An engagement hole 110 is formed in a front end portion 109 of the stopper 104**.

Figure 6:
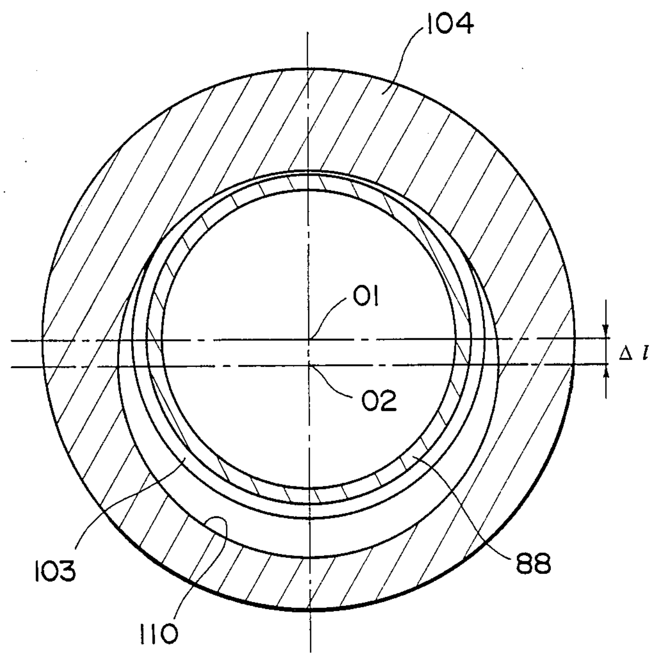
FIG. 6 is an enlarged cross-sectional view taken along line A—A' of FIG. 1.

The engagement hole 110 is, as shown in FIG. 6, formed such that it opens in a circular form with its center located at a position O2 which is biased by an amount from a center axis O1 of the stopper 104. The inner diameter Ls of the engagement hole 110 is selected to be slightly smaller than the maximum diameter of the portion between the end portion 11 and the groove portion 103 (in this case, a diameter Lt of the end portion 11 is the maximum diameter.) Therefore, the engagement hole 110 can be inserted through the end member 11. Thus, the upper portion of the portion of the stopper 104 which has the (eccentric) engagement hole 110 is shifted toward the center axis O1 with respect to the groove portion 103. Thus, the insertion aid 22 is attached to the endoscope 2 with the upper portion of the front end portion 109 engaged with the groove portion 103.

An externally threaded portion 111 on which the cover member 106 is fitted is formed around the outer periphery of the rear end portion of the stopper 104, while an internally threaded portion 112 which is screwed onto the externally threaded portion 111 is formed around the inner periphery of the front end of the cover member 106.

In addition, projecting portions 114, which has a diameter larger than the other portion of the cover member 106, are formed around, for example, the front and rear portions of the cover member 106 in the longitudinal direction. Since the projecting portions 114 are provided in this manner, it is possible to prevent the inserting section 6 from being biased toward a portion of a tube wall even when the inserting section 6 is inserted into a tube having a diameter larger than the inserting section 6.

The inner diameter Ls of the engagement hole 110 of the stopper 104 is selected to be slightly smaller than the maximum outer diameter La of the optical end adapter 21. Thus, in a state wherein the optical end adapter 21 is attached, even if the state of attachment of the insertion aid 22 is loose compared with the normal state, the optical end adapter 21 is engaged at its maximum diameter portion and is thus prevented from coming off.

The operation of the first embodiment will be described below hereinbelow.

If the insertion aid 22 is to be attached to the endoscope 2, the cover member 106, the stopper support 105 and the stopper 104 are inserted through the end portion 11 in that order in a state wherein the optical end adapter 21 is not attached to the end member 11.

Therefore, if the externally threaded portion 107 of the stopper support 105 is screwed into the internally threaded portion 108 of the stopper 104 in a state wherein a portion of the periphery of the engagement hole 110 of the stopper 104 is engaged with the groove portion 103 of the endoscope 2. FIG. 6 is a cross-sectional view showing the state just described. That is to say, a portion of the periphery of the engagement hole 110 of the stopper 104 is fitted into and engaged with the groove portion 103 of the endoscope 2.

Then, when the optical end adapter 21 is attached to the end member 11, the state shown in FIG. 1 is obtained. In this state, the inner diameter Ls of the engagement hole 110 of the stopper 104 becomes slightly smaller than the outer diameter La of the optical end adapter 21. Since the relationship is $$La > Ls \quad (1)$$

even if the state of attachment of the insertion aid 22 to the insertion-aid mounting portion 14 becomes loose, the insertion aid 22 does not come off as long as the optical end adapter 21 is detached from the end portion 11.

If the optical end adapter is correctly attached, a light blocking portion adjacent to the cutaway portion **26*a* does not appear within the visual field of observation. However, if the state of attachment of the adapter 21 becomes loose, a dark portion 116, shown by a dot line in FIG. 2**, which is formed due to blocking of light appears in a periphery of an endoscopic image (in this case, a square image) displayed on the monitor screen of the color monitor 5. It is, therefore, possible to know that the state of attachment of the adapter 21 is loose compared with the normal state. In this case, the inserting section 6 is removed and the optical end adapter 22 is again tightened until it is correctly attached. That is to say, it is possible to prevent the optical end adapter from coming off.

In order to determine whether or not the dark portion 116 has been created by a dark object, it is sufficient to move the endoscope 2 by a slight amount. More specifically, in the case of a dark object, the position of the displayed image changes, but in the case of the light block portion adjacent to the cutaway portion 26, the position hardly changes. In addition, since the shape of the edge of the dark portion which has appeared on the monitor screen does not change, it is possible to make such a decision.

It is to be noted that whether or not the optical end adapter is correctly attached can be determined owing to the fact that a change appears in the visual field of observation, as well as the fact that illuminating light is blocked or that the screen becomes dark.

With the first embodiment, it is possible to positively prevent the inserting aid 22 from coming off and hence to realize an endoscope apparatus whose safety is high.

Figure 7:
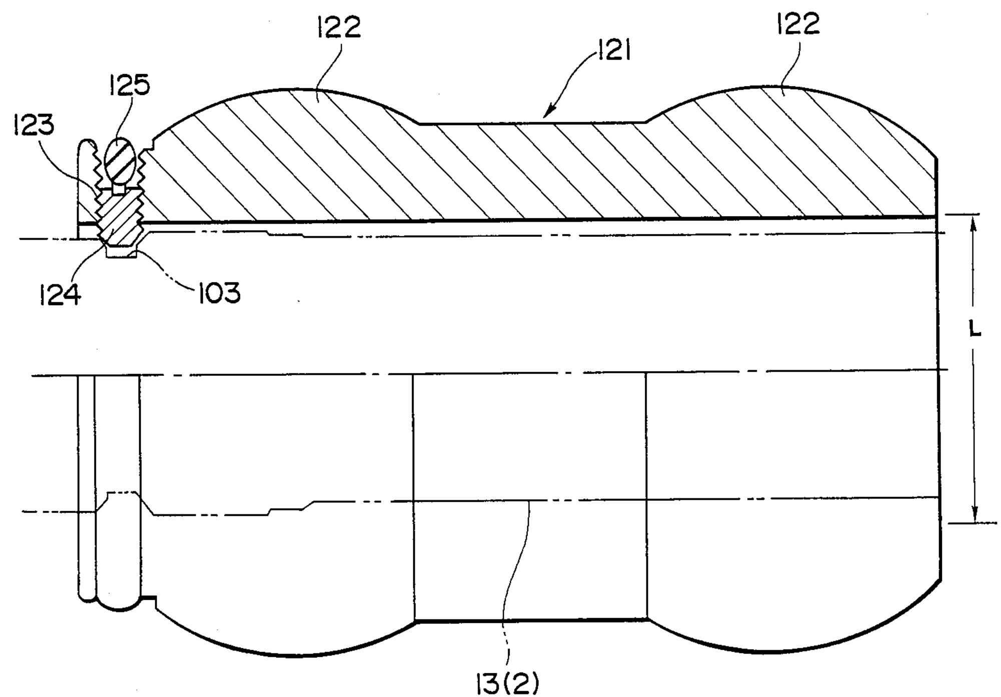
FIG. 7 is a partially cross-sectional view showing the essential portion of a second embodiment of the present invention.

FIG. 7 shows the essential portion of a second embodiment of the present invention.

The embodiment is a modified version of the first embodiment in that the insertion aid 121 shown in FIG. 7 can be attached to the endoscope 2.

The insertion aid 121 has a front projecting portion 122 and a rear projecting portion 122, as in the case of the cover member 106 used in the first embodiment. The inner diameter L of the insertion aid 121 is selected to be slightly smaller than the maximum diameter La of an optical end adapter and to be slightly larger than the maximum diameter Lt of the end member 11. It is to be noted that, there is a case where, even if La=Lt, substantially identical functions can be achieved.

A plurality of threaded holes 123 which radially extend are formed in a front end portion of the insertion aid 121. Screws 124 which are screwed into the respective threaded holes 123 are projected radially inwardly and inserted into (or pressed against) the groove 103 so that the insertion aid 121 can be attached to the endoscope 2. After the screws 124 have been engaged, the outer peripheries of the screws 124 are covered by a screw covering member 125 such as an O ring in order to prevent the screws 124 from coming off.

Figure 8:
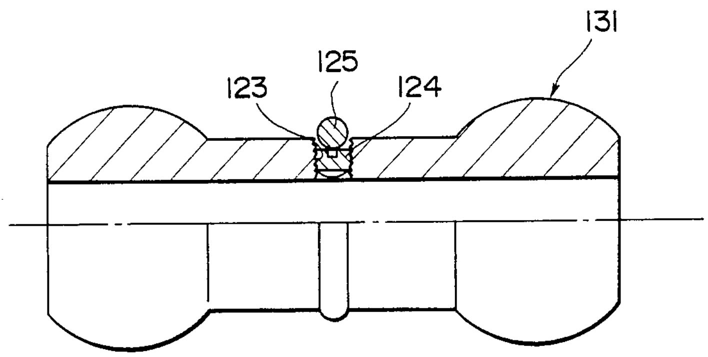
FIG. 8 is a partially cross-sectional view showing the essential portion of a modified form of the second embodiment.

As shown in FIG. 8, in place of the insertion aid 121 shown in FIG. 7, screw holes 123 may be formed in the mid portions of an insertion aid 131 in the longitudinal direction.

In the first embodiment, the stopper support 105 is detachable from the endoscope 2. However, the stopper support 105 may be rotatably provided on the insertion-aid mounting portion 14 so that various kinds of cover members may be attached to the stopper support 105. An externally threaded portion may merely be formed in the insertion aid mounting portion so that various types of aids can be attached to the externally threaded portion.

In a case where the configurations of the outer periphery of the optical end adapter, the outer periphery of the end member, and the inner periphery of the insertion aid are not circular, if a circle circumscribing the configuration or its inscribed circle is regarded as the outer or inner diameter thereof and the relationship between the circumscribed and inscribed circles is selected as indicated by the expression (1), the second embodiment can be applied to endoscopes of various shapes.

Figure 9:
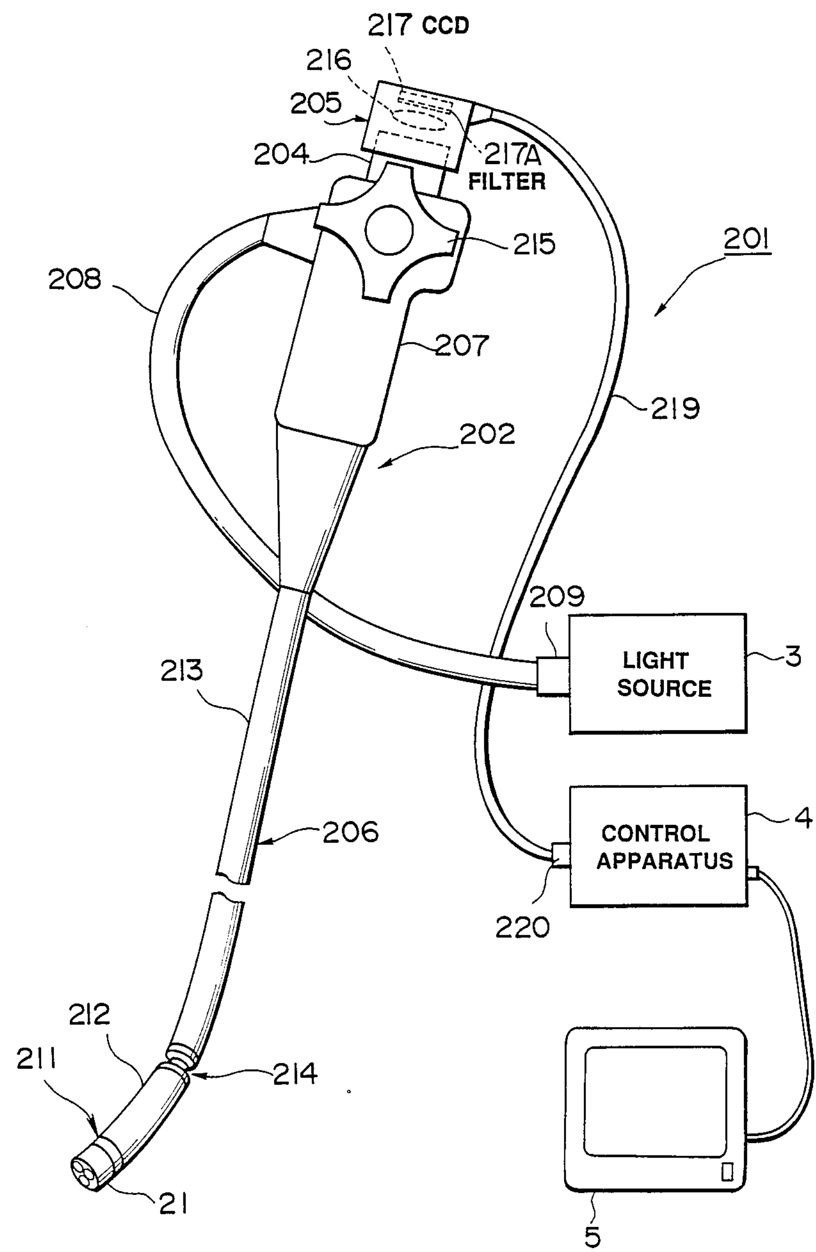
FIG. 9 is a diagrammatic view showing the construction of the whole of an endoscope apparatus according to a third embodiment of the present invention.

FIG. 9 shows an endoscope apparatus according to the third embodiment of the present invention.

An endoscope apparatus 211 is constituted by a fiber scope 202, the light source 3 for supplying illuminating light to the fiber scope 202, the control apparatus 4 for processing the image signals output from a television camera 205, and the color monitor 5 which provides a display of the video signals output from the control apparatus 4.

The fiber scope 202 is constituted by a flexible and elongated inserting section 206, a wide operating section 207 which is formed at the rear end of the inserting section 206, a light guide cable 208 which extends from one side of the operating section 207, and a light guide connector 209 attached to the terminal end of the cable 208, and an eyepiece portion 204 which is formed on the top of the operating section 207.

The front end (the lower end as viewed in FIG. 2) of the inserting section 206 is provided with a hard end member 211, and a flexible section 212 capable of being curved is connected to the rear end of the end member 211 (the upper end as viewed in FIG. 2). A soft section 213 having flexibility is connected to the rear end of the flexible section 212. An insertion-aid mounting portion 214 is provided around the outer periphery of the inserting section 6 which is adjacent to the boundary between the flexible section 212 and the soft section 213.

The flexible section 212 is capable of being freely curved in all directions by operating a curving knob 215 provided on the operating section 207.

Figure 10:
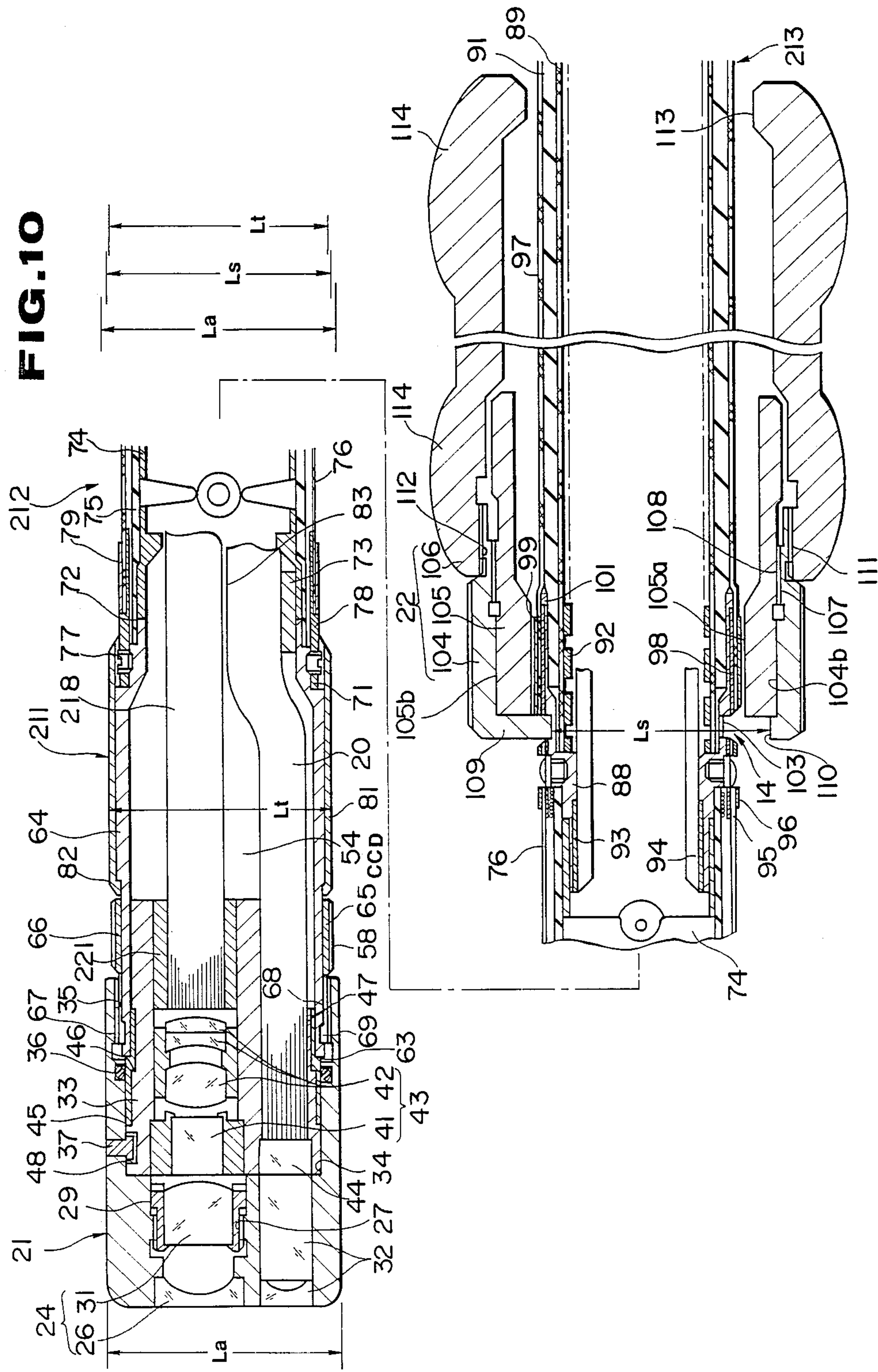
FIG. 10 is a longitudinal sectional view showing the structure of the leading end portion of the inserting section shown in FIG. 9.

The television camera 205 connected to the eyepiece portion 204 accommodates a focusing lens 216 and a CCD 217 and, as shown in FIG. 10, the optical image transmitted through the image guide 218 is focused on the CCD 217. The optical image is subjected to photoelectric conversion, passed through a signal cable 219 and a signal connector 220 provided at the terminal end, and input to the control apparatus 4. In the control apparatus 4, the input signals are processed and reproduced as a color image on the color monitor 5. Although not shown, a mosaic filter 217A is attached to the front surface of the CCD 217 so as to effect color separation for each pixel.

FIG. 10 shows the structure of the front end portion of the fiber scope 202.

The fiber scope 202 is a modified version of the electronic scope 2 shown in FIG. 1 in that the front end surface of the image guide 218 composed of a fiber bundle is fixed in the focal plane of the objective lens system 43 by means of a connector 221.

The structure of the remaining portion is substantially identical to that of the electronic scope 2 and, in FIG. 10, the same reference numerals are used to denote the members which are the same as those used in the electronic scope 2.

In other words, the third embodiment has the structure in which the fiber scope 202 and the television camera 204 are used in place of the electronic endoscope in the first embodiment.

The third embodiment having the above-described structure, of course, has effects and advantages similar to those of the first embodiment.

For example, it is possible to prevent the insertion aid 22 from coming off the optical end adapter 21. If the state of attachment of the adapter 21 becomes loose, an operator can easily know that fact since a dark portion appears in the visual field of observation or in a displayed image.

In addition, since the engagement hole 110 is formed at an eccentric position, as in the first embodiment, the front end portion 109 projects toward the center axis with respect to the groove portion 103. Accordingly, the insertion aid 22 can be attached to the fiber scope 202 with the front end portion 109 caught up in the groove portion 103. Accordingly, since the attachment portion 14 is formed as the groove portion 103, it is possible to attach the insertion aid 22 without the need to increase the outer diameter of the inserting section 206 and without the risk of damaging the inserting section 206.

If a plurality of cover members 106 of various kinds each having a different outer diameter are prepared in advance, it is possible to image various objects which differ in inner diameter.

Figure 11:
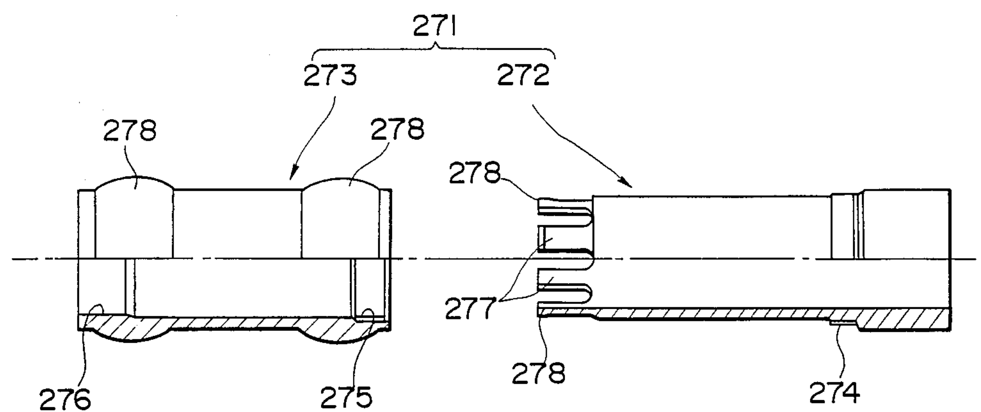
FIG. 11 is a partially cross-sectional view showing the structure of an endoscope insertion aid according to a fourth embodiment of the present invention.

FIG. 11 shows an insertion aid 271 according to a fourth embodiment of the present invention.

The insertion aid 271 according to the fourth embodiment is constituted by a stopper 272 and a cover member 273.

The stopper 272 is constituted by a cylindrical member which can be fitted onto the inserting section 6 from the end portion 11 (as shown in, for example, FIG. 1), and an externally threaded portion 274 is formed around the outer periphery of the the stopper 272 which is adjacent to its end to be attached to the inserting section 6. An internally threaded portion 275 is formed around the inner periphery of one end portion of the cover member 273 so that the internally threaded portion 275 may be screwed onto the externally threaded portion 274. The inner periphery of the rear end portion of the cover member 273 (opposite to the externally threaded portion 275) is formed into a small diameter portion 276 whose inner diameter is reduced. A plurality of cantilever-like projections 277 are formed in the rear end portion (if attached to the inserting section 6, the front end portion) of the stopper 272 which corresponds to the small diameter portion 276 when the cover member 273 is attached. The projecting end of each of the projections 277 has a small projection 278 which projects radially outwardly. The outer diameter of the circle circumscribing the small projections 278 is selected to be larger than the inner diameter of the small diameter portion 276 of the cover member 273. Accordingly, if the small projections 278 are formed to be located over the groove portion 103 when the cover member 273 is attached, the small diameter portion 276 presses the small projections 278 radially inwardly. Thus, the projecting ends of the respective projections 277 are squeezed and engaged with the groove portion 103. Accordingly, the insertion aid 271 can be attached in a manner similar to that used in the first embodiment. The external configuration of the portions of the cover member 273 which are respectively adjacent to, for example, the longitudinal opposite ends are formed into swollen portions 278.

Figure 12:
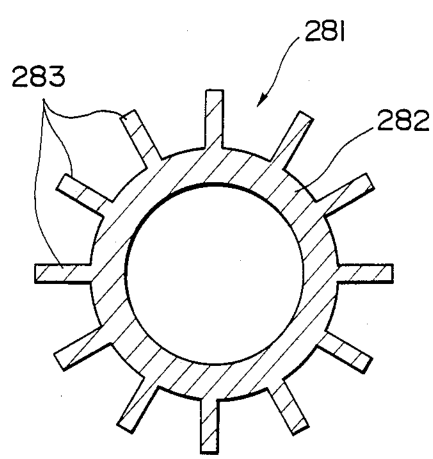
FIG. 12 is a cross-sectional view of a cover member according to a fifth embodiment of the present invention.

FIG. 12 shows a cover member 281 according to a fifth embodiment of the present invention.

In the fifth embodiment, the cover member 281 has the structure that radially extending projections 283 are formed on, for example, the outer periphery of a cylindrical portion 282.

The portion of the cover member 281 which comes into contact with the inner periphery of a portion into which the endoscope apparatus is inserted may be composed of a wheel. Furthermore, an arbitrary member of any shape and structure that serve to aid in inserting the inserting section of the endoscope may be employed.

Figure 13:
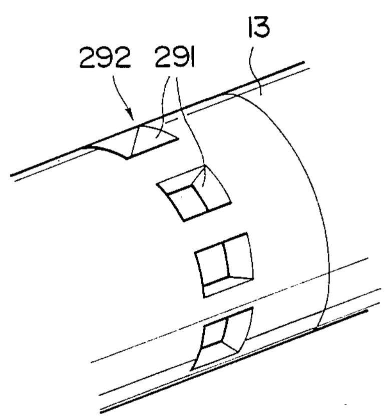
FIG. 13 is a perspective view showing an insertion-aid connecting portion according to a sixth embodiment of the present invention.

The attachment means which is formed in the inserting section 6 is not limited to the groove portion 103 which is formed around the entire periphery. For example, as shown in FIG. 13, a connecting section 292 may be used in which recesses 291 are formed at predetermined intervals around the circumference (in order to hold an insertion aid). In this arrangement, for example, the insertion aid 271 shown in FIG. 12 may be engaged with the recesses 291. It is to be noted that the connecting section 292 may be formed at another location.

Figure 14:
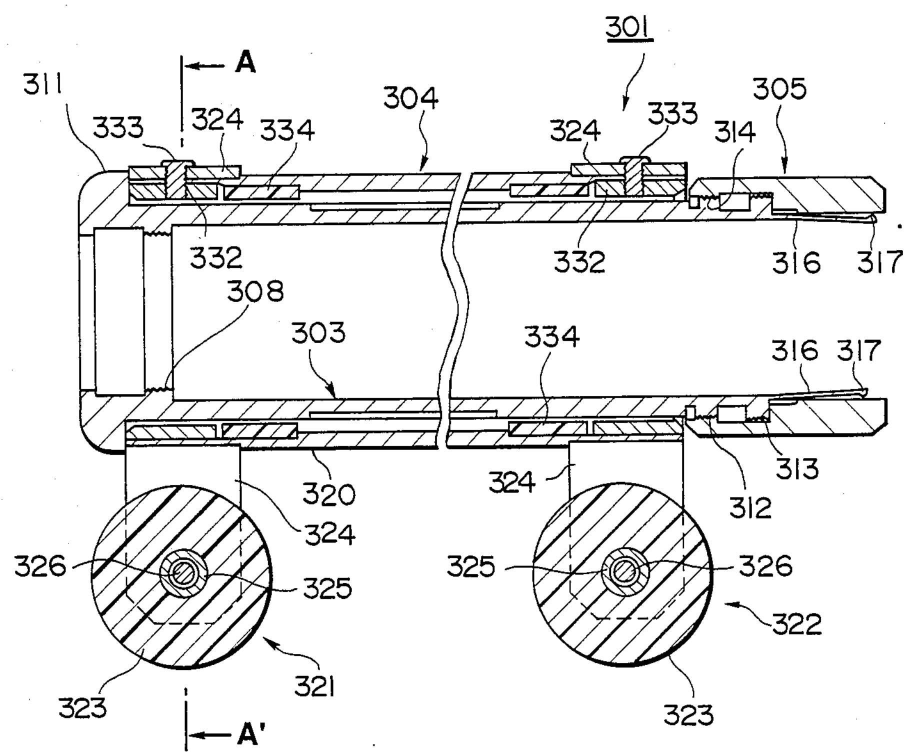
FIG. 14 is a diagrammatic longitudinal sectional view showing the structure of an endoscope insertion aid according to a seventh embodiment of the present invention.
Figure 15:
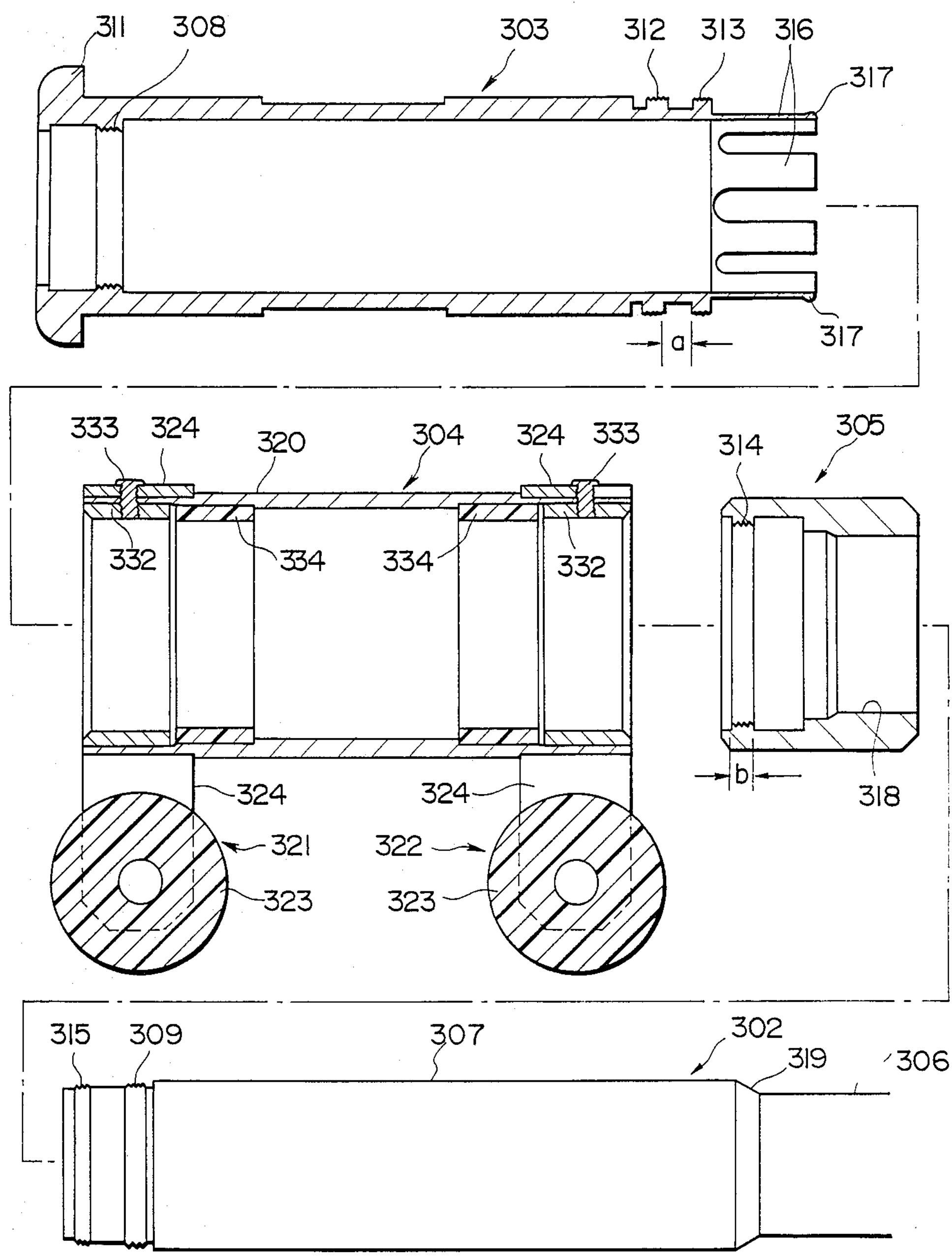
FIG. 15 is an exploded sectional view showing the endoscope insertion aid shown in FIG. 14.

FIGS. 14 and 15 show an endoscope insertion aid according to a seventh embodiment of the present invention.

As shown in FIGS. 14 and 15, an endoscope insertion aid 301 according to the seventh embodiment is constituted by a holding section 303 attached to the front end portion of an endoscope 302, an insertion guide section 304 rotatably disposed with respect to the holding section 303, and a positioning section 305 having a positioning function and the securing function of preventing the insertion guide section 304 fitted onto the holding section 303 from coming off the same.

The holding section 303 can be detachably attached to an end portion 307 of an elongated inserting section 306 of the endoscope 302. More specifically, the holding section 303 is made from a cylindrical member having an inner diameter large enough to engage with the outer diameter of the end portion 307 of the endoscope 302, and an internally threaded portion 308 is formed around an inner periphery of the holding section 303 adjacent to the front end thereof. An externally threaded portion 309 is formed around an outer periphery of the endoscope 302 which is adjacent to the front end of the end portion 307. The internally threaded portion 308 can be screwed onto the externally threaded portion 309. Accordingly, the holding section 303 is fitted onto the end portion 307 of the endoscope 302 from the front end of the end portion 307 until the externally threaded portion 308 comes into contact with the internally threaded portion 309. If the holding section 303 is rotated at the position where the internally threaded portion 308 makes contact with the externally threaded portion 309, both the threaded portions 308 and 309 are engaged with each other so that the holding section 303 can be fixed to the end portion 307 of the endoscope 302. If the direction of rotation is reversed, the holding section 303 can be removed from the end portion 307 of the endoscope 302.

A flange 311 is formed around the outer periphery of the front end of the holding section 303, and the insertion guide section 304 which is fitted onto the outer periphery of the holding section 303 comes into contact with a corresponding step of the flange 311 and is thus held in position. Two externally threaded portions 312 and 313 are formed around an outer periphery of the holding section 303 which is adjacent to the rear end thereof, and these threaded portions 312 and 313 are spaced apart at an interval of a (as shown in FIG. 2). An internally threaded portion 314 is formed around a positioning section 305 at locations corresponding to the externally threaded portions 312 and 313. If the internally threaded portion 314 has a width of b with respect to the interval a between the threaded portions 312 and 313, the relationship between a and b is selected to be a>b (for example, a=3 mm; b=2 mm).

Accordingly, if the positioning section 305 is attached to the holding section 303 from the rear thereof, the internally threaded portion 314 is first screwed onto the externally threaded portion 312, then unscrewed from the externally threaded portion 312 in the area between the externally threaded portions 312 and 313, and then screwed onto the other externally threaded portion 312. Since such a double-screw structure is adopted, even if the engagement between the externally threaded portion 312 and the internally threaded portion 314 becomes loose and they are disengaged from each other while the inserting section 306 of the endoscope 302 is being moved in a tube, the internally threaded portion 314 is placed in an idling state at a location between the externally threaded portions 312 and 313. As a result, the internally threaded portion 314 does not easily engage with the externally threaded portion 313. Accordingly, it is possible to prevent the insertion guide section 304 fitted onto the holding section 303 from coming off the same in the tube and therefore to improve safety.

For the same reasons as described above, the internally threaded portion 308 is formed around the inner periphery of the holding section 303 which is adjacent to the front end thereof, and the externally threaded portion 309 and an externally threaded portion 315 at the front thereof are formed around the outer periphery of the end portion 307 which is adjacent to the front end thereof. Thus, a double-screw structure is realized with respect to the internally threaded portion 308.

It is to be noted that a detachable connection mechanism is formed in which the holding section 303 is easily separated from the insertion guide section 304 by unscrewing (from the holding section 303) the positioning section 305 which is screwed onto the rear end of the holding section 303.

A plurality of elongated cutouts are formed in the rear end portion of the holding section 303 and thus a plurality of cantilever-shaped projections 316 are formed. The projecting end of each of the projections 316 has a small projection 317 which projects radially outwardly. The outer diameter of the circle circumscribing the small projections 317 is selected to be larger than an inner diameter portion 318 formed in a rear portion of the positioning section 305.

As shown in FIG. 15, the outer periphery of the rear end portion of the end portion 307 of the endoscope 302 is formed into a tapered portion 319 whose outer periphery is of conical shape. The outer diameter of the end portion 307 is selected to be larger than that of the inserting section 306 which extends from the rear end of the end portion 307.

When the positioning section 305 is attached to the holding section 303, the inner diameter portion 318 presses the small projections 317 radially inwardly, and thus the ends of the respective projections 316 are squeezed inwardly. The projecting ends of the respective projections thus squeezed are capable of engaging with the tapered portion 319 of the end portion 307 of the inserting section 306. Accordingly, even if the enmeshment between the internally threaded portion 314 of the holding section 303 and the externally threaded portion 309 of the end portion 307 of the inserting section 306 becomes loose when the insertion aid 301 is attached, it is possible to prevent the end portion 307 from coming off the insertion aid 301.

As shown in FIG. 15, the insertion guide section 304 can be fitted onto the holding section 303 from the rear thereof. When the positioning section 305 is screwed onto the rear portion of the holding section 304 after the insertion guide section 304 has been attached, the insertion guide section 304 is supported for rotation with respect to the holding section 304. That is to say, a rotatable supporting mechanism is provided.

The insertion section 304 is constituted by an outer pipe 320 of cylindrical shape and wheels 321 and 322 which are respectively attached to the outer peripheries of the outer pipe 320 which are respectively adjacent to the front and rear ends thereof. The provision of the wheels 321 and 322 enable the inserting section 306 to be moved in an object to be examined smoothly and without the risk of damaging the object.

Figure 16:
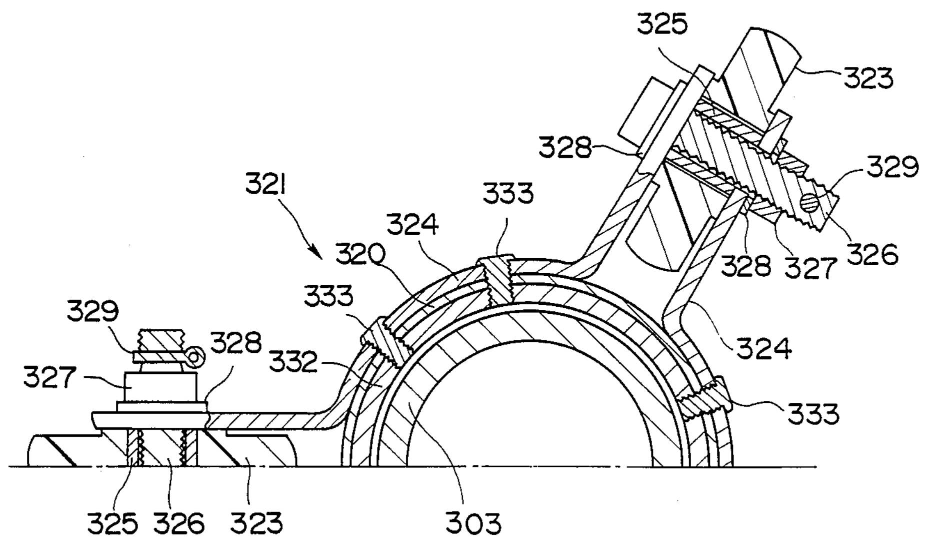
FIG. 16 is an enlarged sectional view taken along line A—A' of FIG. 14.

Each of the wheels 321 and 322 has the same structure and, in this embodiment, has three wheels 323 which are disposed in the circumferential direction as shown in FIG. 16 (two of them are shown in FIG. 16.) Each of the wheels 323 is composed of a disk-shaped member made of a synthesized polymer material such as a plastic or rubber, and is rotatably supported by two arms 324 which extend radially outwardly and in parallel with each other.

Since each of the wheels 323 is formed of a synthesized polymer material whose hardness is not too high, the wheels 323 do not damage an object to be examined while they are rolling in the object.

A through-hole is formed in each of the wheels 323 along the axis of rotation thereof, and a collar 352 having an outer diameter which is slightly smaller than the outer diameter of the through-hole is inserted into the through-hole (therefore, the wheel 323 is rotatable about the collar 325). Then, the wheel 323 is sandwiched between the two parallel arms 324, a bolt 326 is inserted through the hollow portion of the collar 325 and the corresponding holes in the respective arms 324, and a nut is screwed onto the bolt 326. Thus, each of the wheels 323 is rotatably attached. In FIG. 16, reference numerals 328 denote washers.

The length of each of the collar 325 is selected to be approximately equal to the width of the wheel 323, and the gap between the parallel arms 324 is determined by the collar 325 so that the wheel 323 is sandwiched therebetween. Accordingly, the wheel 323 is not depressed to such an extent that its width becomes smaller than the length of the collar 325, and hence the wheel 323 is supported for rotation about the collar 325.

After the bolt 326 is fastened by the nut 327, a pin 329 is fitted into a hole in the portion of the bolt 326 which projects from the nut 327 so that the nut 327 does not come off the bolt 326 even if the nut 327 becomes loose.

Each of the arms 324 for supporting the wheels 323 is fixed as follows: an arcuated portion of each of the arms 324 is overlapped upon the outer periphery of a front or rear thin wall of an outer pipe 320 which constitutes the inserting section 4, while an annular screw holding member 332 is overlapped upon the inner periphery of the thin wall, the arcuated portion and the holding member 332 being fixed to each other by means of screws 333.

In order to improve the sliding function required between rotary sliding portions of the insertion guide section 304 and the holding section 303, an annular sliding member 334 made of a plastic material is, as shown in FIGS. 15 or 14, fitted into the inserting section 304 at locations adjacent to, for example, the respective screw holding member 332. More specifically, the diameters of the inner peripheries of the outer pipes 320 which are adjacent to the respective screw holding members 332 are selected to be slightly larger than the inner diameter of the intermediate portion of the outer pipe 320. The respective sliding members 334 whose outer diameter is approximately equal to the above inner diameter are fitted into the outer pipe 320. Subsequently, the annular screw holding members 332 each having an inner diameter slightly larger than that of the adjacent sliding member 344 are respectively fitted into the opposite ends of the inserting guide section 304, and each of the screw holding members 332 is screwed as described above. The inner diameter of each of the sliding members 334 is slightly larger than the outer diameter of the holding section 303 which is fitted into it. Accordingly the sliding members 334 are slidably and rotatably fitted into the holding section and the insertion guide section 304 (the outer pipe 320). The above-described sliding members 334 are fitted between the insertion guide section 304 and the holding section 303 and constitute a rotatable slide joint section which provides relative smooth rotation. It is to be noted that the sliding members 334 are preferably made of a material exhibiting a low friction coefficient with respect to a member which constitutes the outer periphery of the holding section 303 located within the sliding members 334. For example, Teflon (a fluoro resin such as polytetrafluoroethylene or the like) may be used. (The sliding members 334 may be constituted by roller bearings such as ball bearings.)

A plurality of insertion guide sections 304 of different types each of which, for example, has a different amount of outward projection can be detachably attached to an identical holding section 303.

In accordance with the seventh embodiment which is constructed in the above-described manner, when the insertion aid 302 is to be attached to the end portion 307 of the endoscope 302 as shown in FIG. 15, if, for example, the engagement between the externally threaded portions 312 and 313 formed around the rear end portion of the holding section 303 is released by rotating the positioning section 305, the end portion 307 of the endoscope 302 can be inserted into the insertion aid 301. Subsequently, when either the insertion aid 301 or the endoscope 302 is rotated with respect to the other, the internally threaded portion 308 formed around the inner periphery of the front end portion of the holding section 303 can be screwed onto the externally threaded portion 309 formed around the outer periphery of the front end portion of the holding section 303. Subsequently, when the positioning section 305 which has been loosened is rotated and screwed onto the holding section 303, the holding section 303 can be easily attached to the endoscope 302. If the holding section 303 is to be detached from the endoscope 302, the positioning section 305 is unscrewed and then either the endoscope 302 or the insertion aid 301 is rotated. Thus, the holding section 303 can be detached.

The holding section 303 can be attached to and detached from the endoscope 302 by such an easy operation.

As described above, the seventh embodiment is constituted by three members; the holding section 303 which can be attached to and detached from the end portion 307 of the endoscope 302 by screwing, the insertion guide section 304 which can be fitted onto the outer periphery of the holding section 303, and the positioning section 305 which is then screwed onto the insertion guide section 304 to fix the insertion guide section 304 and prevent it from the holding section 303. A rolling means which is capable of rolling in an object to be examined is provided on the outer periphery of the insertion guide section 304. Accordingly, if the end portion of an endoscope provided with the seventh embodiment is inserted into, for example, a tube which is bent, since the rolling means which can roll and travel is provided on the outer periphery of the insertion guide section 304, the end portion can be smoothly moved toward a portion to be examined. In this case, since the rolling portion is made from a plastic member whose hardness is low, the inner wall of the tube is not damaged. Even if a rotary twisting force is applied to the endoscope when it is being moved or the direction of observation is changed, no rotational force is applied to the insertion guide section 304 and the portion of the insertion guide section 304 which is in contact with the inner wall of the tube hardly slides laterally, since the insertion guide section 304 is rotatably supported by the holding section 303 to which the endoscope 302 is attached. Accordingly, the inner wall of a tube or the like is not damaged due to lateral sliding which has took place in the conventional arrangements.

While the inserting section 306 is moving in a portion of a tube which contains a large amount of dust, sand, metal powder or the like, it may enter the inserting section 306. However, since the positioning section 305 can be unscrewed to slide, in the axial direction, the insertion guide section 304 fitted onto the holding section 303. Accordingly, it is possible to easily eliminate dust or the like from the rotatable slide joint portions.

In addition, if the inserting section 306 is to be inserted into a tube having a different inner diameter, the insertion guide section 304 can be easily removed and replaced with an insertion guide section of size matching the inner diameter or the like of a desired tube.

Figure 17:
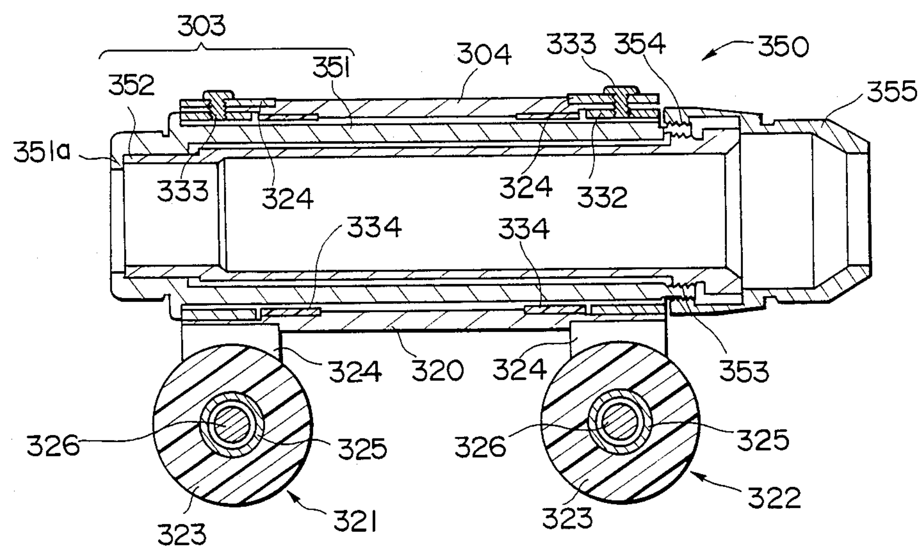
FIG. 17 is a longitudinal sectional view of a modified form of the endoscope insertion aid according to the seventh embodiment of the present invention.

FIG. 17 shows an endoscope insertion aid 350 according to a modified form of the seventh embodiment of the present invention.

This modified form is characterized in that the holding section used in the seventh embodiment shown in FIGS. 15 and 16 is constituted by a stopper 351 and a stopper support 352.

The rear end of the stopper support 352 has an externally threaded portion 353 which is screwed into a corresponding internally threaded portion of the stopper 351. The stopper 351 is removably screwed onto the outer peirphery of the stopper support 352.

An externally threaded portion 354 is formed around the outer periphery of the rear end of the stopper 351 so that a positioning portion 355 can be attached by screwing.

The remaining construction of the sixth embodiment is substantially identical to that of the seventh embodiment and, therefore, the same elements are denoted by the same reference numerals.

In order to attach the endoscope insertion aid 350 to an endoscope, a projection **251*a* which projects radially inwardly at the front end of the stopper 351 is brought into engagement with, for example, the groove 103 of the endoscope 2 according to the first embodiment, and thus the projection 351*a* is caught up by the wall of the groove 103**.

It is to be noted that the insertion guide section 304 is detachable from the stopper 351 if the positioning section 355 is removed. The insertion guide section 304 is rotatably disposed with respect to the holding section 303 (or the stopper 351), as in the seventh embodiment.

Figure 18:
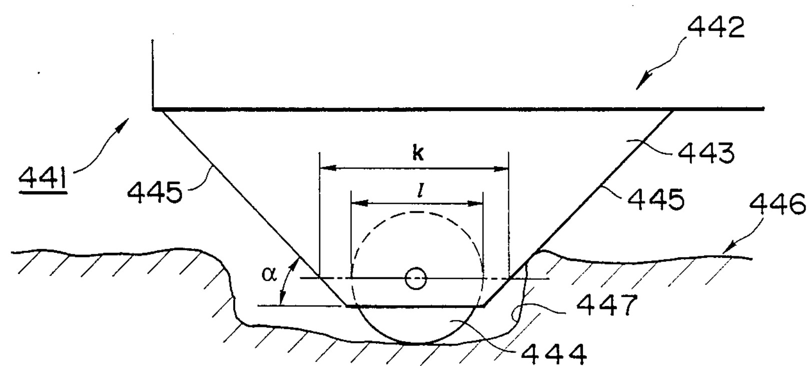
FIG. 18 is a schematic side elevational view of the essential portion of an endoscope insertion aid according to an eighth embodiment.

FIG. 18 shows the essential portion of an eighth embodiment of the present invention.

As shown in FIG. 18, an insertion aid 441 according to the eighth embodiment is formed into a trapezoidal shape so that each arm 443 provided on an insertion guide section 442 makes an angle of $\alpha$ with respect to the axis of the insertion guide section 44.

The angle is selected within a range of $0<\alpha<90$ degrees and, in this embodiment, the angle $\alpha$ is 45 degrees. A slope 445 is formed such that the arm 443 becomes gradually wide from the side of the wheel 444 to the base of the arm 443. Accordingly, if the length k of a line which passes through the axis of rotation of the wheel 444 in parallel with the axis of the insertion aid 441 and which crosses the opposite slopes 445 and the diameter l of the wheel 444 are selected so that the relationship of $k<l$ is established, even if there is a depression 447 or a similar step in a portion 446 to be examined, and if the insertion aid 441 is caught up in the depression 447, the wheel 444 can be moved out of it by a moving operation, no matter how deep the depression 447 may be.

The eighth embodiment is similar to the seventh embodiment except that the configuration of the arm 443 differs from that of the arm used in the seventh embodiment. FIG. 17 shows, for example, the one, among the arms 443, which is provided adjacent to the front end of the insertion guide section 441, but, although not shown, the arms 443 provided in the other portions are the same as the illustrated one.

A different embodiment can be constructed by combining portions of the respective embodiments of the present invention.

What is claimed is:

1. An electronic endoscope comprising:

an endoscope including an elongated inserting section and an inserting end portion provided at the leading end of said inserting section and having a leading end surface provided with an illuminating window through which illuminating light is projected onto an object to be observed and an observation window for receiving light reflected from said object for the purposes of observation;

an optical adapter having a first optical element which is detachably mounted on a first mounting portion provided on the outer periphery of said inserting end portion and mounted in opposed relationship with said illuminating window and a second optical element mounted in opposed relationship with said observation window;

an endoscope insertion aid capable of being mounted on a second mounting portion provided on the outer periphery of said inserting section which is disposed rearwardly of said first mounting portion of said inserting end section, said endoscope insertion aid projecting outwardly from the outer periphery of said inserting section so as to aid said inserting section to be inserted; and means for preventing said endoscope insertion aid from coming off, said means being formed such that its minimum effective inner diameter does not exceed the maximum effective inner diameter of said optical adapter.

2. An apparatus according to claim 1, wherein said first mounting portion is a mechanism which can be attached and detached by rotating operation and which is arranged so that if the state of attachment of said first mounting portion becomes loose, at least one of the opposing relationships between said illuminating window and said first optical element and between said observation window and said second optical element is changed so that a dark portion appears in an endoscopic image obtained by observation through said observation window.

3. An apparatus according to claim 1 or 2, wherein said second mounting portion is constituted by a groove portion which is provided around the outer periphery of said inserting section.

4. An apparatus according to claim 3, wherein said endoscope insertion aid has a projection which can engage with said groove portion.

5. An apparatus according to claim 1 or 2, wherein said second mounting portion is constituted by a plurality of recesses which are provided at predetermined intervals around the outer periphery of said inserting section.

6. An apparatus according to claim 3, wherein said endoscope insertion aid has an approximately cylindrical configuration which includes a hollow portion through which said inserting end portion is inserted, the minimum effective diameter of said projection being selected with the center thereof corresponding to a position eccentric with respect to the center line of said hollow portion.

7. An apparatus according to claim 4, wherein said projection is a screw which can be freely protruded radially inwardly from said endoscope insertion aid.

8. An apparatus according to claim 1 or 2, wherein said endoscope insertion aid is constituted by a holding member which can be attached to said inserting end portion and a cover member which can be attached to the outer periphery of said holding member and which projects radially inwardly.

9. An apparatus according to claim 8, wherein said cover member has a wheel which serves to aid said inserting section to be inserted.

10. An apparatus according to claim 8, wherein said cover member is disposed for rotation with respect to said holding member.

11. An apparatus according to claim 10, wherein a positioning member which serves to define the longitudinal movement of said cover member can be attached to the rear end of said holding member.

12. An apparatus according to claim 8, wherein said cover member has an approximately cylindrical configuration and a plurality of projections of approximately constant effective diameter which are formed on its outer periphery along the longitudinal axis thereof.

13. An apparatus according to claim 1 or 2, wherein said endoscope is an electronic endoscope whose solid state imaging device is disposed in the focal plane of an objective optical system which is disposed ahead of said observation window.

14. An apparatus according to claim 1 or 2, wherein said endoscope is a fiber scope including an image guide formed from a fiber bundle, the leading end surface of said image guide being disposed in the focal plane of an objective optical system which is disposed ahead of said observation window.

15. An apparatus according to claim 14 further comprising a television camera which is attached to said fiber scope, said television camera including a solid state imaging device.

16. An apparatus according to claim 13 further comprising signal processing means for processing the image signals obtained by imaging in said electronic endoscope and a color monitor arranged to reproduce a color image from the standard video signals generated by said signal processing means.

17. An apparatus according to claim 16, wherein said dark portion can be displayed on said color monitor.

* * * * *